United States Patent [19]

de Solms et al.

[11] Patent Number: 5,504,212
[45] Date of Patent: * Apr. 2, 1996

[54] INHIBITORS OF FARNESYL-PROTEIN TRANSFERASE

[75] Inventors: S. Jane de Solms, Norristown; Samuel L. Graham, Schwneksville; John S. Wai, Harleysville, all of Pa.

[73] Assignee: Merck & Co., Inc., Rahway, N.J.

[*] Notice: The portion of the term of this patent subsequent to Nov. 28, 2012, has been disclaimed.

[21] Appl. No.: 968,022

[22] Filed: Oct. 29, 1992

[51] Int. Cl.$^6$ .................... C07D 213/28; C07C 229/00
[52] U.S. Cl. ................... 546/336; 548/338.5; 562/444; 562/556; 562/557
[58] Field of Search ................... 564/162, 197; 546/335; 548/341, 338.5; 560/557, 559; 562/444, 556, 557

[56] References Cited

U.S. PATENT DOCUMENTS

| | | | |
|---|---|---|---|
| 5,043,268 | 8/1991 | Stock | 435/15 |
| 5,141,851 | 8/1992 | Brown | 435/15 |

FOREIGN PATENT DOCUMENTS

| | | |
|---|---|---|
| 0456180A1 | 11/1991 | European Pat. Off. . |
| 91/16340 | 10/1991 | WIPO . |

OTHER PUBLICATIONS

Kohl, N. E. et al., "Protein farnsyltransferase inhibitors block the growth of ras–dependent tumors in nude mice", Proc. Natl. Acad. Sci. USA, vol. 91, pp. 9141–1945 (1994).
Goldstein, J. L., et al., "Nonfarnesylated Tetrapeptide Inhibitors of Protein Farnesyltransferase", *The Journal of Biological Chemistry*, vol. 266, No. 24, pp. 15575–15578 (1991).

*Primary Examiner*—C. Warren Ivy
*Assistant Examiner*—A. A. Owens
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

5 Claims, No Drawings

INHIBITORS OF FARNESYL-PROTEIN TRANSFERASE

BACKGROUND OF THE INVENTION

The Ras gene is found activated in many human cancers, including colorectal carcinoma, exocrine pancreatic carcinoma, and myeloid leukemias. Forms of Ras in cancer cells have mutations that distinguish the protein from Ras in normal cells. Biological and biochemical studies of Ras action indicate that Ras functions like a G-regulatory protein, since Ras must be localized in the plasma membrane and must bind with GTP in order to transform cells (Gibbs, J. et al., *Microbiol. Rev.* 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Aaa is an aliphatic amino acid, the Xaa is any amino acid) (Willumsen et al., *Nature* 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., *Cell* 57:1167 (1989); Casey et al., *Proc. Natl. Acad. Sci. USA* 86:8323 (1989)). In addition, Ha-Ras and N-Ras are palmitoylated via formation of a thioester on a Cys residue near a C-terminal Cys farnesyl acceptor (Gutierrez et al., *EMBO J.* 8:1093–1098 (1989); Hancock et al., *Cell* 57: 1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., *J. Biol. Chem.* 263:18236 (1988); Farnsworth et al., *J. Biol. Chem.* 264:20422 (1989)).

Inhibition of Ras farnesylation in vivo has been demonstrated with lovastatin (Merck & Co., Rahway, N.J.) and compactin (Hancock et al, ibid; Casey et al., ibid; Schafer et al., *Science* 245:379 (1989)). These drugs inhibit EMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., *Cell,* 62:81–88 (1990); Schaber et al., *J. Biol. Chem.,* 265:14701–14704 (1990); Schafer et al., *Science,* 249: 1133–1139 (1990); Manne et al., *Proc. Natl. Acad. Sci USA,* 87:7541–7545 (1990)).

Inhibition of farnesyl-protein transferase and, thereby, of farnesylation of the Ras protein, blocks the ability of Ras to transform normal cells to cancer cells. The compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa$^1$-Aaa$^2$-Xaa box membrane domain present) and activated (impaired GTPase activity, staying bound to GTP) form of Ras acts as a dominant negative Ras inhibitor of membrane-bound Ras function (Gibbs et al., *Proc. Natl. Acad. Sci. USA* 86:6630–6634(1989)). Cytosol localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects resulting from interference with other metabolic processes which utilize the enzyme.

These compounds and their analogs are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides containing cysteine as an amino terminal residue with the CAAX sequence inhibit Ras farnesylation (Schaber et al., ibid; Reiss et. al., ibid; Reiss et al., *PNAS* 88:732–736 (1991)). Such inhibitors may inhibit while serving as alternate substrates for the Ras farnesyl-transferase enzyme, or may be purely competitive inhibitors (U.S. Pat. No. 5,141, 851, University of Texas).

Peptide analogs containing one or more reduced peptide bonds and of the general structure C-Xaa$^1$-(ΨCH$_2$NH)Xaa$^2$–Xaa$^3$ where C is cysteine and Xaa$^{1-2}$ is any amino acid and Xaa$^3$ is either homoserine or methionine are inhibitors of ras farnesyl transferase. However, the presence of the reduced amide linkage, (ΨCH$_2$NH), renders these inhibitors unstable with respect to the formation of the corresponding diketopiperazines, which are significantly less active against ras farnesyl transferase, thus limiting efficacy in vivo.

Substitution of the causative nitrogen with non-nucleophilic carbon leads to active ras farnesyl transferase inhibitors which do not form diketopiperazines. Conformational constraint in the form of trans olefin at this position leads to more potent inhibitors. These inhibitors are competitive and reversible, and will not be farnesylated by the enzyme.

It is, therefore, an object of this invention to develop peptide analogs containing carbon isosteres at one or more of their peptide bonds which will inhibit farnesyl-protein transferase and the farnesylation of the oncogene protein Ras. It is a further object of this invention to develop chemotherapeutic compositions containing the compounds of this invention, and methods for producing the compounds of this invention.

SUMMARY OF THE INVENTION

The present invention includes compounds which inhibit farnesyl-protein transferase and the farnesylation of the oncogene protein Ras, chemotherapeutic compositions containing the compounds of this invention, and methods for producing the compounds of this invention.

The compounds of this invention are illustrated by the formulae:

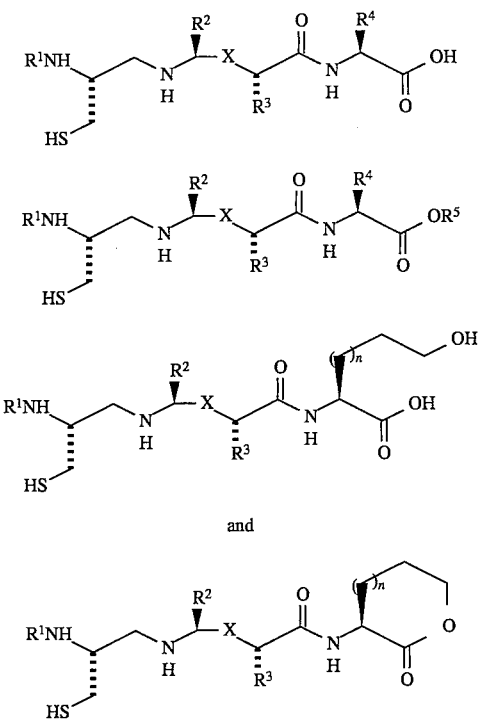

and

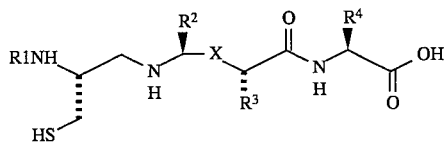

wherein:
X is $CH_2CH_2$ or trans $CH=CH$

DETAILED DESCRIPTION OF THE INVENTION

The compounds of this invention are useful in the inhibition of farnesyl-protein transferase and the farnesylation of the oncogene protein Ras. In a first embodiment of this invention the inhibitors of farnesyl-protein transferase are illustrated by the formula I:

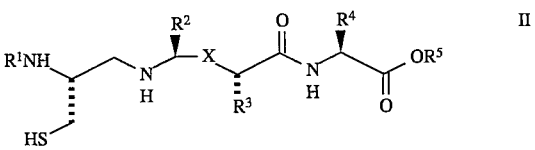

wherein:
$R^1$ is hydrogen, an alkyl group, an aralkyl group, an acyl group, an aracyl group, an aroyl group, an alkylsulfonyl group, aralkylsulfonyl group or arylsulfonyl group, wherein the alkyl and the alkyl portion of the acyl is a straight chain or branched chain hydrocarbons of 1 to 6 carbon atoms;

$R^2$, $R^3$ and $R^4$ are the side chains of naturally occuring amino acids, including their oxidized forms which may be methionine sulfoxide or methionine sulfone, or in the alternative may be substituted or unsubstititued aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

X is $CH_2CH_2$ or trans $CH=CH$;
and the pharmaceutically acceptable salts thereof.

In a second embodiment of this invention, the prodrugs of compounds of formula I are illustrated by the formula II:

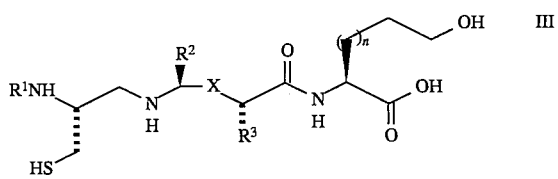

wherein:
$R^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

$R^2$, $R^3$ and $R^4$ are the side chains of naturally occuring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic zing;

$R^5$ is a substituted or unsubstituted aliphatic, aromatic or heteroaromatic group such as a saturated chain of 1 to 8 carbon atoms, which may be branched or unbranched, wherein the aliphatic substituent may be substituted with an aromatic or heteroaromatic ring;

X is $CH_2CH_2$ or trans $CH=CH$;
and the pharmaceutically acceptable salts and disulfides thereof.

In a third embodiment of this invention, the inhibitors of farnesyl-protein transferase are illustrated by the formula III:

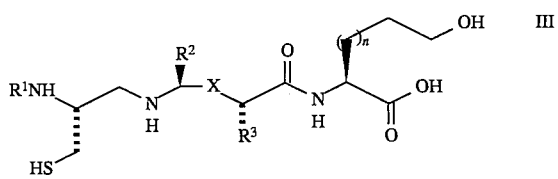

wherein:
$R^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

$R^2$ and $R^3$ are the side chains of naturally occuring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted with an aromatic or heteroaromatic ring;

X is $CH_2CH_2$ or trans $CH=CH$;
n is 0, 1 or 2;
and the pharmaceutically acceptable salts thereof.

In a fourth embodiment of this invention, the prodrugs of compounds of formula III are illustrated by the formula IV:

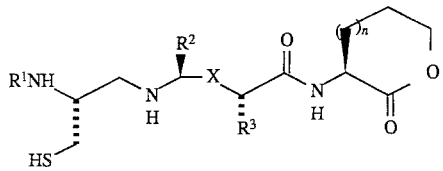

wherein:

$R^1$ is hydrogen, an alkyl group, an aralkyl group, an acyl group, an aracyl group, an aroyl group, an alkylsulfonyl group, aralkylsulfonyl group or arylsulfonyl group, wherein alkyl and acyl groups comprise straight chain or branched chain hydrocarbons of 1 to 6 carbon atoms;

$R^2$ and $R^3$ are the side chains of naturally occuring amino acids, including their oxidized forms which may be methionine sulfoxide or methionine sulfone, or in the alternative may be substituted or unsubstituted aliphatic, aromatic or heteroaromatic groups, such as allyl, cyclohexyl, phenyl, pyridyl, imidazolyl or saturated chains of 2 to 8 carbon atoms which may be branched or unbranched, wherein the aliphatic substituents may be substituted With an aromatic or heteroaromatic ring;

X is $CH_2CH_2$ or trans $CH=CH$;

n is 0, 1 or 2;

and the pharmaceutically acceptable salts and disulfides thereof.

The preferred compounds of this invention are as follows:

5(S)-[2(R)-amino-3-mercaptopropylamino]-6(S)-methyl-2(R)-n-propyl-3,4-E-octenoyl-homoserine, and the corresponding homoserine lactone, 5(S)-[2(R)-amino-3-mercaptopropylamino]-6(S)-methyl-2(R)-methyl-3,4-E-octenoyl-homoserine, and the corresponding homoserine lactone, 5(S)-[2(R)-amino-3-mercaptopropylamino]-6(S)-methyl-2(R)-ethyl-3,4-E-octenoyl-homoserine, and the corresponding homoserine lactone, 5(S)-[2(R)-amino-3-mercaptopropylamino]-6(S)-methyl-2(R)-i-propyl-3,4-E-octenoyl-homoserine, and the corresponding homoserine lactone, 5(S)-[2(R)-amino-3-mercaptopropylamino]-6(S)-methyl-2(R)-n-butyl-3,4-E-octenoyl-homoserine, and the corresponding homoserine lactone, (S)-[2(R)-amino-3-mercaptopropylamino]-6(S)-methyl-2(R)-s-butyl-3,4-E-octenoyl-homoserine, and the corresponding homoserine lactone, 5(S)-[2(R)-amino-3-mercaptopropylamino]-6(S)-methyl-2(R)-t-butyl-3,4-E-octenoyl-homoserine, and the corresponding homoserine lactone, 5(S)-[2(R)-amino-3-mercaptopropylamino]-6(S)-methyl-2(R)-cyclohexyl-3,4-E-octenoyl-homoserine, and the corresponding homoserine lactone, 5(S)-[2(R)-amino-3-mercaptopropylamino]-6(S)-methyl-2(R)-cyclopentyl-3,4-E-octenoyl-homoserine, and the corresponding homoserine lactone, 5(S)-[2(R)-amino-3-mercaptopropylamino]-6(S)-methyl-2(R)-benzyl-3,4-E-octenoyl-homoserine, and the corresponding homoserine lactone, 5(S)-[2(R)-amino-3-mercaptopropylamino]-6-methyl-2(R)-i-propyl-3,4-E-heptenoyl-homoserine, and the corresponding homoserine lactone, 5(S)-[2(R)-amino-3-mercaptopropylamino]-6(S)-methyl-2(R)-i-propyl-3,4-E-octenoyl-methionine, and the corresponding methyl ester, 5(S)-[2(R)-amino-3-mercaptopropylamino]-6(S)-methyl-2(R)-n-butyl-3,4-E-octenoyl-methionine, and the corresponding methyl ester, 5(S)-[2(R)-amino-3-mercaptopropylamino]-6(S)-methyl-2-(R)-benzyl-3,4-E-octenoyl-methionine, and the corresponding methyl ester, 5(S)-[2(R)-amino-3-mercaptopropylamino]-6(S)-methyl-2(R)-n-propyl-octanoyl-homoserine, and the corresponding homoserine lactone, 5(S)-[2(R)-amino-3-mercaptopropylamino]-6(S)-methyl-2(R)-benzyl-octanoyl-homoserine, and the corresponding homoserine lactone, and the pharmaceutically acceptable salts thereof.

In the more preferred embodiment, the invention is comprised of the following inhibitors and the corresponding lactones or methyl esters:

5(S)-[2(R)-amino-3-mercaptopropylamino]-6(S)-methyl-2(R)-n-propyl-3,4-E-octenoyl-homoserine, 5(S)-[2(R)-amino-3-mercaptopropylamino]-6(S)-methyl-2(R)-ethyl-3,4-E-octenoyl-homoserine, 5(S)-[2(R)-amino-3-mercaptopropylamino]-6(S)-methyl-2(R)-i-propyl-3,4-E-octenoyl-homoserine, 5(S)-[2(R)-amino-3-mercaptopropylamino]-6(S)-methyl-2(R)-n-butyl-3,4-E-octenoyl-homoserine, 5(S)-[2(R)-amino-3-mercaptopropylamino]-6(S)-methyl-2(R)-s-butyl-3,4-E-octenoyl-homoserine, 5(S)-[2(R)-amino-3-mercaptopropylamino]-6(S)-methyl-2(R) -benzyl-3,4-E-octenoyl-homoserine, 5(S)-[2(R)-amino-3-mercaptopropylamino]-6-methyl-2(R)-i-propyl-3,4-E-heptenoyl-homoserine, 5(S)-[2(R)-amino-3-mercaptopropylamino]-6(S)-methyl-2(R)-n-butyl-3,4-E-octenoyl-methionine, 5(S)-[2(R)-amino-3-mercaptopropylamino]-6(S)-methyl-2(R)-benzyl-3,4-E-octenoyl-methionine, 5(S)-[2(R)-amino-3-mercaptopropylamino]-6(S)-methyl-2(R)-i-propyl-3,4-E-octenoyl-methionine, and the pharmaceutically acceptable salts thereof.

In the most preferred embodiment, the invention is comprised of the following inhibitors and the corresponding lactones or methyl esters:

5(S)-[2(R)-amino-3-mercaptopropylamino]-6(S)-methyl-2(R)-benzyl-3,4-E-octenoyl-methionine

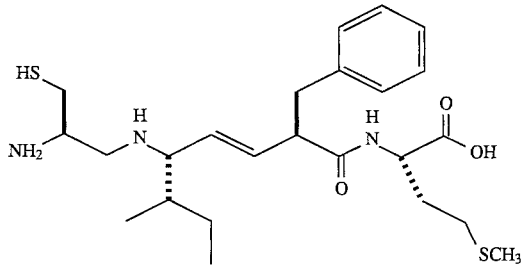

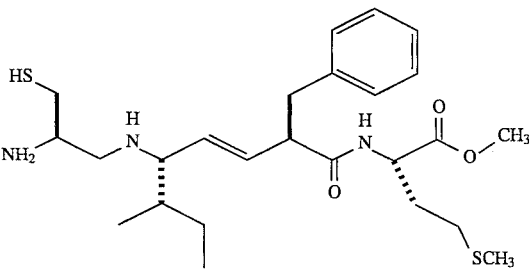

5(S)-[2(R)-amino-3-mercaptopropylamino]-6(S)-methyl-2(R)-i-propyl-3,4-E-octenoyl-homoserine

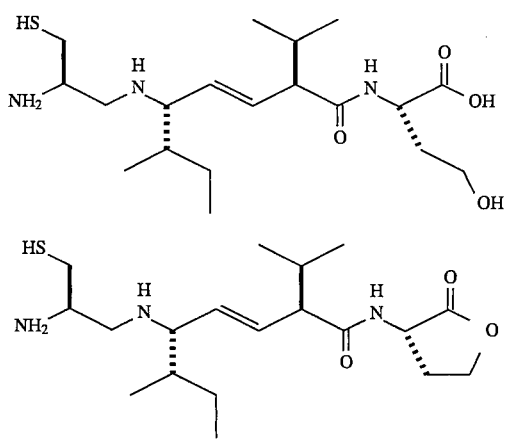

5(S)-[2(R)-amino-3-mercaptopropylamino]-6(S)-methyl-2(R)-n-butyl-3,4-E-octenoyl-methionine

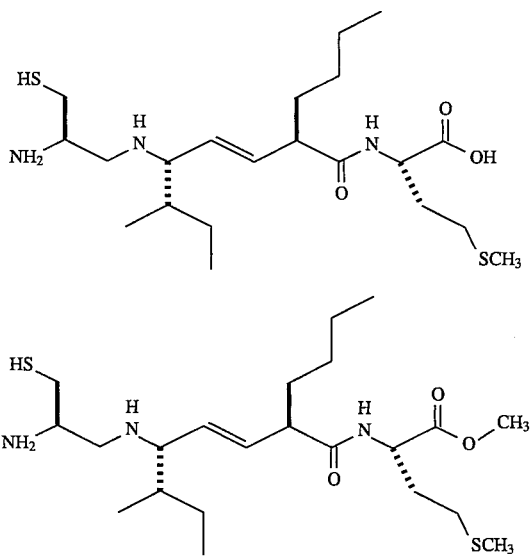

5(S)-[2(R)-amino-3-mercaptopropylamino]-6-methyl-2(R)-i-propyl-3,4-E-hepenoyl-homoserine

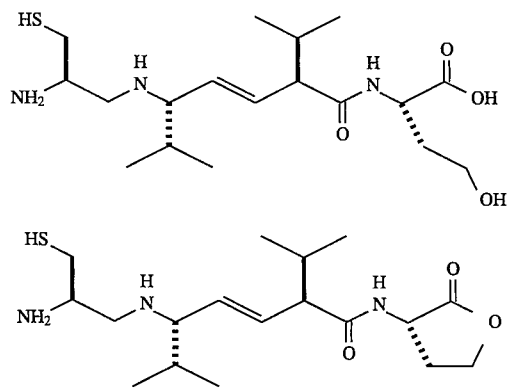

5(S)-[2(R)-amino-3-mercaptopropylamino]-6(S)-methyl-2(R)i-propyl-3,4-E-octenoyl-methionine

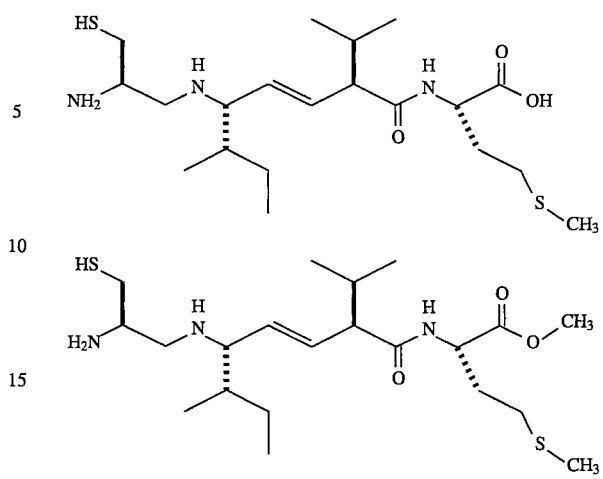

and the pharmaceutically acceptable salts thereof.

The carboxyl terminal residue of the compounds of formulae I and III as exemplified is either homoserine or methionine. However, a number of amino acids would be expected to provide potent FTase inhibitors. Examples of such carboxy terminal residues would include, but are not limited to, glutamine, methionine sulfone, and serine.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared by reacting the free base with stoichiometric amounts or with an excess of the desired salt-forming inorganic or organic acid in a suitable solvent or various combinations of solvents.

The compounds of the invention can be synthesized from their constituent amino acids by conventional peptide synthesis techniques, and the additional methods described below. Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980, or Stewart et al., "Solid Phase Peptide Synthesis", Second Edition, Pierce Chemical Company, 1984. The teachings of these works are hereby incorporated by reference.

The compounds of this invention are prepared by employing the reaction sequences shown in Schemes I and II. Scheme I outlines the preparation of the alkene isosteres utilizing standard manipulations such as Weinreb amide formation, Grignard reaction, acetylation, ozonolysis, Wittig reaction, ester hydrolysis, peptide coupling reaction, mesylation, cleavage of peptide protecting groups, reductive alkylation, etc., as may be known in the literature or exemplified in the Experimental Procedure. The key reactions are: stereoselective reduction of the Boc-amino-enone to the corresponding syn amino-alcohol (Scheme 1, Step B, Part 1), and stereospecific boron triflouride or zinc chloride activated organo-magnesio, organo-lithio, or organo-zinc copper(l) cyanide $S_N2'$ displacement reaction (Scheme I, Step G). Through the use of optically pure N-Boc amino acids as starting material and these two key reactions, the stereochemistry of the final products is well defined. The alkane analogs are prepared in a similar manner by including an additional catalytic hydrogenation step as outlined in Scheme II.

REACTION SCHEME I

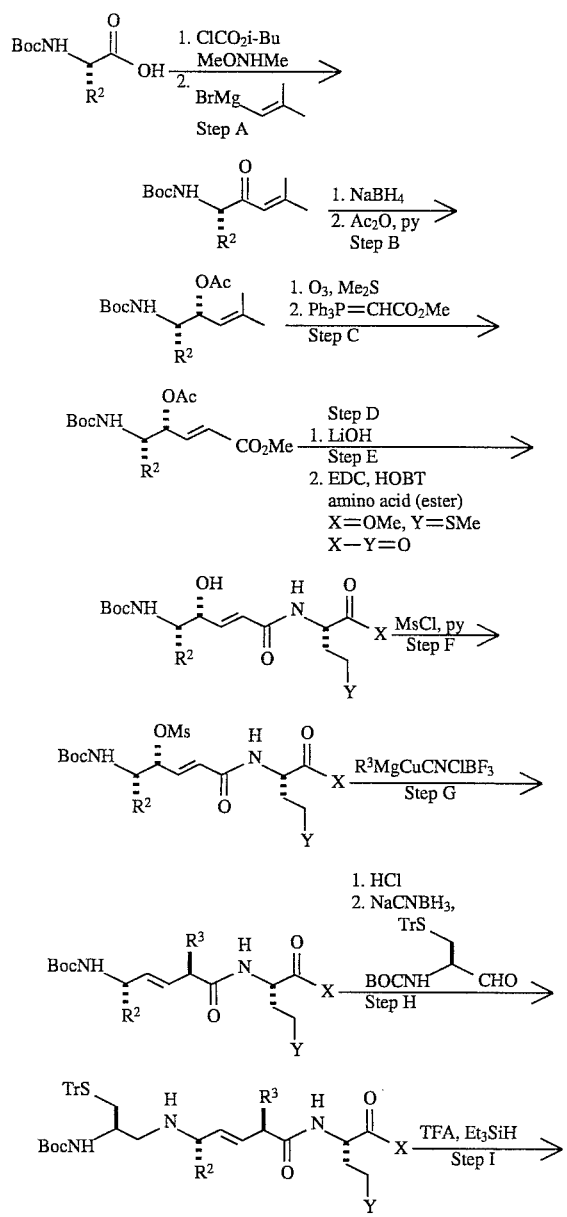

-continued
REACTION SCHEME I

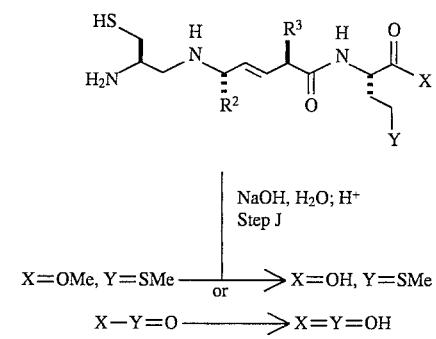

REACTION SCHEME II

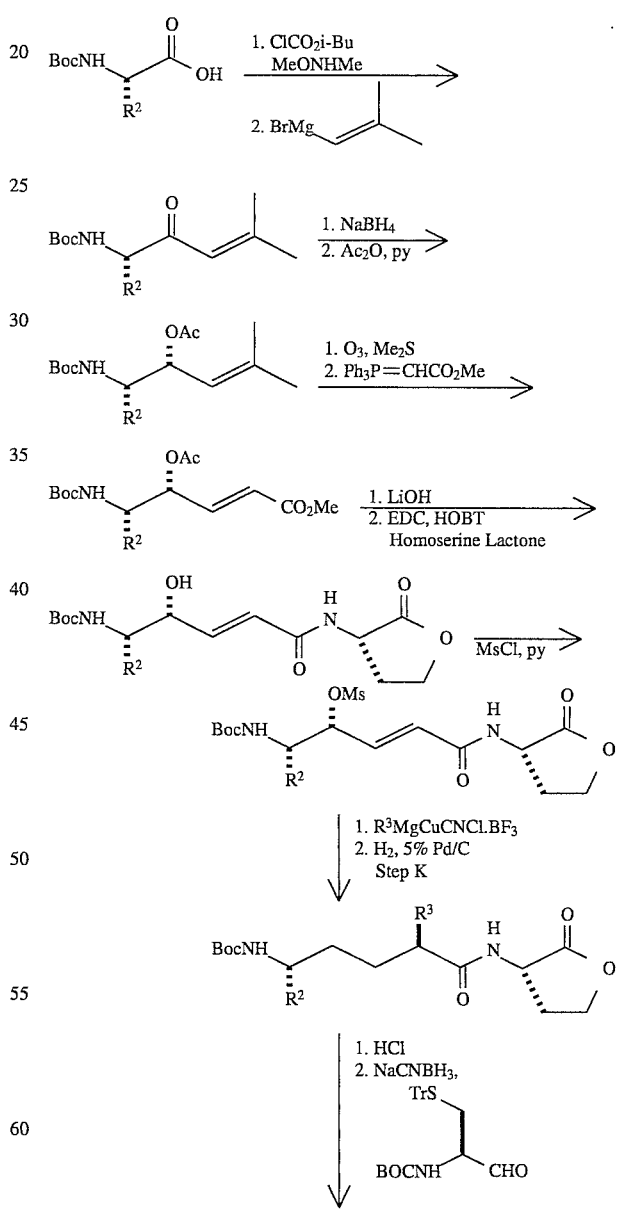

-continued
REACTION SCHEME II

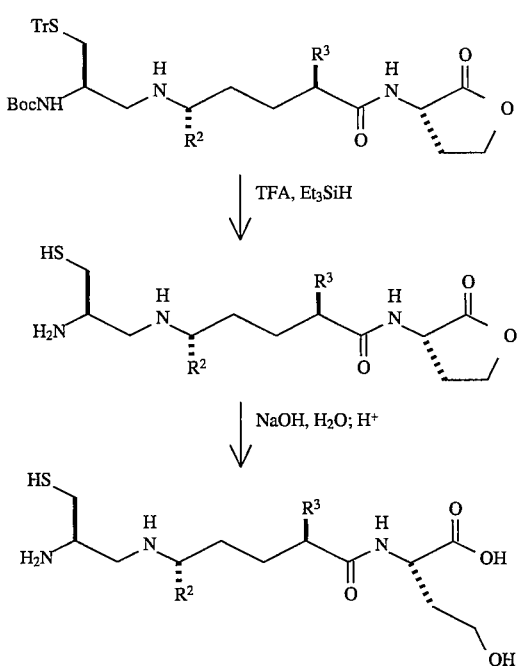

The compounds of this invention inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous, rectal and topical administration.

For oral use of a chemotherapeutic compound according to this invention, the selected compound may be administered, for example, in-the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about. 0.1 mg/kg of body weight to about 20 mg/kg of body weight per day, preferably of between 0.5 mg/kg of body weight to about 10 mg/kg of body weight per day.

EXAMPLES

Examples provided are intended to assist in a further understanding of the invention. Particular materials employed, species and conditions are intended to be further illustrative of the invention and not limitative of the reasonable scope thereof.

Example 1

Preparation of 5(S)-[2(R)-amino-3-mercaptopropylamino]-6(S)-methyl-2(R)-n-propyl-3, 4-E-octenyl-homoserine lactone and 5(S)-[2(R)-amino-3-mercaptopropylamino]- 6(S)-methyl-2(R)-n-propyl-3,4-E-octenoyl-homoserine Step A. Preparation of 4(S)-N-tert-(butyloxy)carbonyl-amino-3(S),7,dimethyl-6,7-octen-5-one To a cold (0° C.) solution of N-t-(butoxy)carbonyl-L-isoleucine hemihydrate (6.01 g, 25 mmol) in ethyl acetate (90 mL), N-methyl morpholine (2.75 mL, 25 mmol) and isobutyl chloroformate (3.25 mL, 25.1 mmol) were added successively. The resultant white suspension was stirred at 0° C. for 15 minutes treated with N,O-dimethylhydroxylamine hydrochloride (2.52 g, 25.8 mmol) and N-methylmorpholine (2.75 mL, 25 mmol), and then stirred at room temperature overnight. The resultant mixture was washed successively with water, 10% aqueous citric acid, brine, and was dried over anhydrous magnesium sulfate, filtered and concentrated. The residual oil was chromatographed on silica gel eluting with 30% ethyl acetate in hexane. Collection and concentration of appropriate fractions provided 5.0 g (73%) of the corresponding amide.

A 1 liter three neck round bottom flask was charged with magnesium turnings (44 g, 1.8 mol) and flamed dried under a steady stream of dry argon. The turnings were activated by stirring under an atmosphere of argon for an additional 3 to 4 hours at room temperature. Tetrahydrofuran (450 mL), freshly distilled from sodium benzophenone ketyl, 2-methylpropenyl bromide (50 g, 0.37 mol), and a crystal of iodine were added. The mixture was warmed gently with a mantle until slight reflux occurred. Without removing the mantle heating was discontinued, and the mixture was stirred overnight under an atmosphere of argon. The resultant Grignard reagent was used as described in the following.

To a cold (–50° C.) solution of N-tert-(butyloxy)carbonyl-isoleucine N,O-dimethylhydroxylamide (17.2 g, 63 mmol) in tetrahydrofuran (400 mL), the above Grignard reagent in tetrahydrofuran (prepared from 50 g of 2-methylpropenyl bromide) was added over a period of 20 min., with the temperature of the reacting solution maintained below −40° C. The mixture was then allowed to warm up slowly to room temperature. The resultant solution was diluted with diethyl ether, treated with 10% aqueous citric acid, washed with brine, dried over magnesium sulfate, filtered, and concentrated under vacuo. The residual oil was chromatographed on silica gel eluting with 7% ethyl acetate in hexane. Collection and concentration of appropriate fractions provided 12.6 g (74%) of the ketone.

Step B. Preparation of 4(S)-N-tert-(butyloxy)carbonylamino-5(R)-acetoxy-3(S),7-dimethyl-6,7-octene To a cold (0° C.) solution of 4(S)-N-tert-(butyloxy)carbonylamino-3(S),7-dimethyl-6,7-octen-5one (12.57 g, 46.7 mmol) in methanol (200 mL), sodium borohydride was added portionwise until reaction was complete as monitored by TLC on silica gel eluting with 20% ethyl acetate in hexane. The resultant mixture was concentrated under vacuo. The residue was suspended in diethyl ether, washed successively with 1M aqueous hydrochloric acid and brine, dried over magnesium sulfate, filtered and concentrated under vacuo to provide the corresponding alcohol (11.93 g).

Without further purification, the crude alcohol, 4-N,N-dimethyl-aminopyridine (0.132 g), and pyridine (17 mL) were dissolved in dichloromethane (48 mL), cooled to 0° C. and treated with acetic anhydride (18.8 mL, 199 mmol). The resultant mixture was stirred at room temp for 2 hours and concentrated under vacuo. The residual oil was chromatographed on silica gel eluting with 20% ethyl acetate in hexane. Collection and concentration of appropriate fractions provided 10.7 g (73%) of the acetate as a white solid.

Step C. Preparation of methyl 5(S)-N-tert-(butyloxy)-carbonylamino-4(R)-acetoxy-6(S)-methyl-2,3-E-octenoate To a cold (−78° C.) solution of 4(S)-N-tert-(butyloxy)carbonylamino-5(R)-acetoxy-3(S),7-dimethyl-6, 7,-octene (6.5 g, 20.7 mmol) in dichloromethane (100 mL), a steady stream of ozone was bubbled through until a blue color persisted. The mixture was stirred for an additional 5 min and purge with argon to remove excess ozone. Then dimethyl sulfide (15 mL) was added and the reaction mixture was allowed to warm to room temperature. The resultant mixture was cooled back to −78° C., and (carbomethoxymethylene)triphenylphosphorane (15.3 g, 45.7 mmol) was added. The mixture was stirred at room temp overnight and concentrated onto silica gel (20 g). The resultant solid was loaded on a column of silica gel and the product was eluted with 15% EtOAc in hexane. Collection and concentration of appropriate fractions provided 6.5 (91%) of the octenoate.

Step D. Preparation of 5(S)-N-tert-(butyloxy)carbonylamino-4(R)-hydroxy-6(S)-methyl-2,3-E-octenoic acid To a solution of methyl 5(S)-N-tert-(butyloxy)carbonylamino-4(R)-acetoxy-6(S)-methyl-2,3-E-octenoate (1 g, 2.9 mmol) in tetrahydrofuran (2 mL), a solution of lithium hydroxide (0.5 g, 12 mmol) in methanol-water (3:1 v/v) was added. The mixture was made homogenous by addition of minimum amount of a methanol-water (3:1 v/v) and stirred at room temp for 2 days. The resultant solution was acidified with aqueous hydrochloric acid to pH 5 and concentrated under vacuo. The residue was subjected to column chromatography on silica gel eluting with 20% methanol in chloroform. Collection and concentration of appropriate fraction provided 0.71 g (87%) of the corresponding hydroxy-acid.

Step E. Preparation of 5(S)-N-tert-(butyloxy)carbonylamino-4(R)-hydroxy-6(S)-methyl-2,3-E-octenoyl homoserine lactone To a solution of 5(S)-N-tert-(butyloxy)carbonylamino-4(R)-hydroxy-6(S)-methyl-2,3-E-octenoic acid (0.71g, 2.5 mmol) in dimethyl-formamide (10 mL), 1-(3-dimethylaminopropyl)-3-ethylcarbodiimide hydrochloride (0.58 g, 3 mmol), 1-hydroxybenzotriazole hydrate (0.4 g, 3 mmol), L-homoserine lactone hydrochloride (0.52, 3.7 mmol), and diisopropylethylamine (0.66 mL, 3.7 mmol) were added. The resultant mixture was stirred at room temp. overnight, and concentrated under vacuo. The residue was diluted with ethyl acetate, and the organic solution was washed successively with water, 10% aqueous citric acid and brine; dried over magnesium sulfate; filtered and concentrated. The residue was then subjected to column chromatography on silica gel eluting with 5% methanol in chloroform. Collection and concentration of appropriate fractions provided 0.76 g (82%) of the coupled product.

Step F. Preparation of 5(S)-N-tert-(butyloxy)carbonylamino-4(R)-(methylsulfonyl)oxy-6(S)-methyl-2,3-E-octenoyl homoserine lactone To a cold (−20 ° C.) solution of 5(S)-N-tert-(butyloxy)carbonyl-amino-4(R)-hydroxy-6(S)-methyl-2, 3-E-octenoyl homoserine lactone (0.35 g, 0.94 mmol) in a mixture of dichloromethane (6 mL) and pyridine (3 mL), methanesulfonyl chloride (0.4 mL) was added. The resultant mixture was kept at 0° C. overnight, and concentrated under vacuo. The residue was diluted with dichloromethane, washed successively with satd. sodium bicarbonate and brine. The organic phase was dried over magnesium sulfate, filtered and concentrated. The residue was subjected to column chromatography on silica gel eluting with a mixture of ethyl acetate and hexane, 8:2 v/v. Collection and concentration of appropriate fractions provided 0.3 g (71%) of the mesylate, which is stable for storage at −10° C.

Step G. Preparation of 5(S)-N-tert-(butyloxy)carbonylamino-6(S)-methyl-2(R)-n-propyl-3, 4-E-octenoyl-homoserine lactone To a cold (−78° C.) suspension of copper(I) cyanide (0.28 g, 3.1 mmol) in tetrahydrofuran (30 mL, freshly distilled from sodium benzophenone ketyl), a solution of n-propylmagnesium chloride (1.47 mL, 2.0M, 2.9 mmol) in diethyl ether was added. The mixture was stirred at 0° C. until a homogeneous solution was formed. Once a solution was formed, it was cooled to −78° C., boron-trifluoride etherate (0.36 mL, 2.9 mmol) was added, and the resulting mixture was stirred at −78° C. for 5 minutes. A solution of 5(S)-N-tert-(butyloxy)-carbonyl-amino-4(R)-(methylsulfonyl)-oxy-6 (S)-methyl-2,3-E-octenoyl homoserine lactone (0.33 g, 0.74 mmol) in tetrahydrofuran (25 mL) was added dropwise to the above mixture. The resultant solution was stirred at −78° C. for 2 hours and quenched with saturated aqueous ammonium chloride. Conc. NH₄OH was added to obtain pH=8 and the resulting mixture was extracted with diethyl ether. The organic solution was washed with brine, dried over magnesium sulfate, filtered, and concentrated. The residue was chromatographed on silica gel eluting with 50% ethyl acetate in hexane. Collection and concentration of appropriate fractions provided 0.26 g (93%) of the 3,4-E-octenoyl-homoserine.

Step H. 5(S)-[2(R)-N-tert-(butyloxy)carbonylamino-3-S-triphenylmethylmercapto-propylamino]-6 (S)-methyl-2(R)-n-propyl-3,4-E-octenoyl-homoserine lactone To a cold (0° C.) solution of 5(S)-N-tert-(butyloxy)carbonylamino-6(S)-methyl-2(R)-n-propyl-3, 4-E-octenoyl-homoserine (0.26 g, 0.68 mmol) in a mixture of ethyl acetate (30 mL) and dichloromethane (30 mL), a steady stream of anhydrous hydrogen chloride gas was bubbled through for a period of 20 min. The mixture was capped and stirred for an additional 30 min at 0° C. The resultant solution was than purged with a stream of argon and concentrated under vacuo to provide the corresponding hydrochloride salt (0.24 g).

To a mixture of the crude hydrochloride (0.24 g), N-tert-(butyloxy)carbonyl-S-triphenylmethyl-L-cysteine aldehyde [0.57 g, 1.64 mmol, prepared according to the procedure of Goel, Krolls, Stier, and Kesten Org. Syn, 67 69–74 (1988)], molecular sieves (3A° , powder) and methanol (5 mL), (pH adjusted to 6 by addition of diisopropylethylamine at room temp), sodium cyanoborohydride (62 mg, 1 mmol) was added. The resultant slurry was stirred overnight, filtered and concentrated. The residue was diluted with ethyl acetate, .washed with brine, dried over magnesium sulfate, filtered, and concentrated under vacuo. The residue was chromatographed on silica gel eluting with 1.5% methanol in chloroform to afford 283 mg (24%) of the coupled product.

Step I. Preparation of 5(S)-[2(R)-amino-3-mercaptopropylamino]-6(S)-methyl-2(R)-n-propyl-3, 4-E-octenoyl-homoserine lactone To a solution of 5(S)-[2(R)-N-tert-(butyloxy)-carbonylamino-3-S-triphenylmethylmercapto-propylamino]- 6(S)-methyl-2(R)-methyl-3,4-E-octenoyl-homoserine lactone (245 mg, 0.34 mmol) in a mixture of dichloromethane (6 mL) and trifluoroacetic acid (3 mL) at room temperature, triethylsilane (217 µL, 1.36 mmol) was added. The resultant solution was stirred at room temperature for 2 hours, and concentrated under vacuo. The residue was dissolved in a mixture of 0.1% aqueous trifluoroacetic acid (5 mL) and hexane (2 mL). The aqueous layer was washed four more times with hexane, stirred under reduced pressure to remove residual hexane, and lyophilized overnight to provide 193 mg of the homoserine lactone as a white solid.

Anal. Calcd for $C_{19}H_{35}O_3N_3S.2.6\ CF_3COOH$:

C, 42.62; H, 5.58; N, 6.16.

Found: C, 42.55; H, 5.68; N, 6.15.

Step J. Preparation of 5(S)-[2(R)-amino-3-mercaptopropylamino]-6(S)-methyl-2(R)-n-propyl-3, 4-E-octenoyl-homoserine To a solution of 5(S)-[2(R)-amino-3-mercaptopropylamino]-6(S)-methyl-2(R)-n-propyl-3, 4-E-octenoyl-homoserine (4.32 mg, 6.33 µmol)-in methanol (50 µL), an aqueous solution of sodium hydroxide (25.3 µL, 1.00M) was added. After standing at room temp for 1 hour, the solution was diluted with methanol to 10 mM. HPLC analysis and $^1H$ NMR spectroscopy confirmed complete conversion of the lactone to the corresponding hydroxy-acid.

Example 2

5(S)-[2(R)-amino-3-mercaptopropylamino]-6(S)-methyl-2(R)-methyl-3,4-E-octenoyl-homoserine lactone and 5(S)[2(R)-amino-3-mercaptopropylamino]-6(S)-methyl-2(R)-methyl-3, 4-E-octenoyl-homoserine The titled compounds were prepared according to the methods of Example 1, substituting methylmagnesium chloride in Step G. The lactone is obtained as a white solid.

Anal. Calcd for $C_{17}H_{31}O_3N_3S.2.5\ CF_3COOH$:

C, 41.12; H, 5.25; N, 6.54.

Found: C, 41.11; H, 5.52; N, 6.77.

The hydroxy-acid was generated in situ as described in Example 1, Step J.

Example 3

5(S)-[2(R)-amino-3-mercaptopropylamino]-6(S)-methyl-2(R)-ethyl-3,4-E-octenoyl-homoserine lactone and 3.5(S)-[2(R)-amino-3-mercaptopzopylamino]-6(S)-methyl-2(R)-ethyl-3, 4-E-octenoyl-homoserine The titled compounds were prepared according to the methods of Example 1, substituting ethylmagnesium chloride in Step G. The lactone is obtained as a white solid.

Anal. Calcd for $C_{18}H_{33}O_3N_3S.2.7\ CF_3COOH$:

C, 41.37; H, 5.30; N, 6.18.

Found: C, 41.30; H, 5.23; N, 6.42.

The hydroxy-acid was generated in situ as described in Example 1, Step 3.

Example 4

5(S)-[2(R)-amino-3-mercaptopropylamino]-6(S)-methyl-2(R)-i-propyl-3,4-E-octenoyl-homoserine lactone and 5(S)-[2(R)-amino-3-mercaptopropylamino]-6(S)-methyl- 2(R)-i-propyl-3,4-E-octenoyl-homoserine The titled compounds were prepared according to the methods of Example 1, substituting isopropyl-magnesium chloride in Step G. The lactone is obtained as a white solid.

Anal. Calcd for $C_{19}H_{35}O_3N_3S.2.3\ CF_3COOH$:

C, 43.76; H, 5.80; N, 6.49.

Found: C, 43.53; H, 5.79; N, 6.70.

The hydroxy-acid was generated in situ as described in Example 1, Step J.

Example 5

5(S)-[2(R)-amino-3-mercaptopropylamino]-6(S)-methyl-2(R)-n-butyl-3,4-E-octenoyl-homoserine lactone and 5(S)-[2(R)-amino-3-mercaptopropylamino]-6(S)-methyl-2(R)-n-butyl-3, 4-E-octenoyl-homoserine The titled compounds were prepared according to the methods of Example 1, substituting n-butylmagnesium chloride in Step G. The lactone is obtained as a white solid.

Anal. Calcd for $C_{20}H_{37}O_3N_3S.2.7\ CF_3COOH$:

C, 43.12; H, 5.66; N, 5.94.

Found: C, 43.11; H, 5.56; N, 6.14.

The hydroxy-acid was generated in situ as described in Example 1, Step J.

Example 6

5(S)-[2(R)-amino-3-mercaptopropylamino]-6(S)-methyl-2(R)-s-butyl-3,4-E-octenoyl-homoserine lactone and 5(S)-[2(R)-amino-3-mercaptopropylamino]-6(S)-methyl-2(R)-s-butyl-3, 4-E-octenoyl-homoserine The titled compounds were prepared according to the methods of Example 1, substituting s-butylmagnesium chloride in Step G. The lactone is obtained as a white solid (a 1:1 mixture of diastereomers which differed at the chiral center on the 2(R)-s-butyl group).

Anal. Calcd for $C_{20}H_{37}O_3N_3S.2.45\ CF_3COOH$:

C, 44.05; H, 5.86; N, 6.19.

Found: C, 43.93; H, 5.95; N, 6.47.

The hydroxy-acids (a 1:1 mixture of diastereomers which differed at the chiral center on the 2(R)-s-butyl group) were generated in situ as described in Example 1, Step J.

Example 7

5(S)-[2(R)-amino-3-mercaptopropylamino]-6(S)-methyl-2(R)-t-butyl-3,4-E-octenoyl-homoserine lactone and 5(S)-[2(R)-amino-3-mercaptopropyl-amino]-6(S)-methyl-2(R)-t-butyl-3, 4-E-octenoyl-homoserine lactone The titled compounds were prepared according to the methods of Example 1, substituting t-butylmagnesium chloride in Step G. The lactone is obtained as a white solid.

Anal. Calcd for $C_{20}H_{37}O_3N_3S.2.25\ CF_3COOH$:

C, 44.85; H, 6.03; N, 6.40.

Found: C, 44.84; H, 6.09; N, 6.78.

The hydroxy-acid was generated in situ as described in Example 1, Step J.

Example 8

5(S)-[2(R)-amino-3-mercaptopropylamino]-6(S)-methyl-2(R)-cyclohexyl-3,4-E-octenoyl-homoserine lactone and 5(S)-[2(R)-amino-3-mercaptopropylamino]-6(S)-methyl- 2(R)-cyclohexyl-3,4-E-octenoyl-homoserine The titled compounds were prepared according to the methods of Example 1, substituting cyclohexylmagnesium chloride in Step G. The lactone is obtained as a white solid.

Anal. Calcd for $C_{22}H_{39}O_3N_3S.6\ CF_3COOH$:

C, 45.24; H, 5.81; N, 5.82.

Found: C, 45.29; H, 5.94; N, 6.03.

The hydroxy-acid was generated in situ as described in Example 1, Step J.

Example 9

5(S)-[2(R)-amino-3-mercaptopropylamino]-6(S)-methyl-2(R)-cyclopentyl-3,4-E-octenoyl-homoserine lactone and (S)-[2(R)-amino-3-mercaptopropylamino]-6(S)-methyl-2(R)-cyclopentyl-3, 4-E-octenoyl-homoserine The titled compounds were prepared according to the methods of Example 1, substituting cyclopentylmagnesium chloride in Step G. The lactone is obtained as a white solid.

Anal. Calcd for $C_{21}H_{37}O_3N_3S.2.5\ CF_3COOH$:

C, 44.83; H, 5.72; N, 6.03.

Found: C, 44.85; H, 5.81; N, 6.19.

The hydroxy-acid was generated in situ as described in Example 1, Step J.

Example 10

5(S)-[2(R)-amino-3-mercaptopropylamino]-6(S)-methyl-2(R)-benzyl-3,4-E-octenoyl-homoserine lactone and 5(S)-[2(R)-amino-3-mercaptopropyl-amino]-6(S)-methyl-2(R)-benzyl-3,4-E-octenoyl-homoserine The titled compounds were prepared according to the methods of Example 1, substituting benzylmagnesium chloride in Step G. The lactone is obtained as a white solid.

Anal. Calcd for $C_{23}H_{35}O_3N_3S.2.35\ CF_3COOH$:

C, 47.42; H, 5.37; N, 5.99.

Found: C, 47.35; H, 5.53; N, 6.20.

The hydroxy-acid was generated in situ as described in Example 1, Step 3.

Example 11

5(S)-[2(R)-amino-3-mercaptopropylamino]-6-methyl-2(R)-i-propyl-3,4-E-heptenoyl-homoserine lactone and 5(S)-[2(R)-amino-3-mercaptopropyl-amino]-6-methyl-2(R)-i-propyl-3, 4E-heptenoyl-homoserine The titled compounds were prepared according to the methods of Example 1, substituting N-t-(butyloxy)-carbonyl-L-valine in Step A and isopropylmagnesium chloride in Step G. The lactone is obtained as a white solid.

Anal. Calcd for $C_{18}H_{33}O_3N_3S.2.2\ CF_3COOH\ \&\ 1.5\ H_2O$:

C, 41.43; H, 5.93; N, 6.47.

Found: C, 42.65; H, 5.57; N, 6.87.

The hydroxy-acid was generated in situ as described in Example 1, Step J.

Example 12

5(S)-[2(R)-amino-3-mercaptopropylamino]-6(S)-methyl-2(R)-i-propyl-3,4-E-octenoyl-methionine, methyl ester and 5(S)-[2(R)-amino-3-mercaptopropylamino]-6(S)-methyl-2(R)-i-propyl,3,4-E-octenoyl-methionine The titled compounds were prepared according to the methods of Example 1, substituting L-methionine methyl ester in Step E and isopropylmagnesium chloride in Step G. The octenoyl-methionine,- methyl ester was obtained as white solid.

Anal. Calcd for $C_{21}H_{41}O_3N_3S.3HCl$:

C, 45.28; H, 7.96; N, 7.54.

Found: C, 45.37; H, 7.82; N, 7.49.

The free acid was generated as described in the following. To a solution of 5(S)-[2(R)-N-tert-(butyloxy)-carbonylamino-3-S-triphenylmethyl-mercaptopropylamino] -6(S)-methyl-2(R)-i-propyl-3,4-E-octenoylmethionine, methyl ester (102 mg, 0.128 mmol) in methanol (1 mL) at room temperature, an aqueous solution of sodium hydroxide (0.52 mL, 1M) was added and stirred at room temp for 6 hours. The resultant solution was acidified to pH 5, and diluted with ethyl acetate. The organic phase was washed brine, dried over magnesium sulfate, filtered and concentrated under vacuo. The residue was chromatographed on silica gel eluting with 10% methanol in chloroform. Collection and concentration of appropriate fractions provided 5(S)-[2(R)-N-tert-(butyloxy)-carbonylamino-3-S-triphenyl methyl-mercapto-propylamino]-6(S)-methyl-2(R)-i-propyl-3,4-E-octenoyl-methionine. The resultant product was deprotected as described in Example 1, Step I. The acid is obtained as a white solid.

Anal. Calcd for $C_{20}H_{39}N_3O_3S_2.1.9\ CF_3COOH\ \&\ 1.3\ H_2O$:

C, 42.43; H, 6.51; N, 6.24.

Found: C, 42.46; H, 6.48; N, 6.17.

Example 13

5(S)-[2(R)-amino-3-mercaptopropylamino]-6(S)-methyl-2(R)-n-butyl-3,4-E-octenoyl-methionine, methyl ester and 5(S)-[2(R)-amino-3-mercaptopropyl-amino]-6(S)-methyl-2(R)-n-butyl-3,4-E- octenoyl-methionine

The titled compounds were prepared according to the methods of Example 1, substituting L-methionine methyl ester in Step E and n-butyl-magnesium chloride in Step G. The octenoyl-methionine methyl ester was obtained as white solid.

Anal. Calcd for $C_{22}H_{43}O_3N_3S_2 \cdot 2.8HCl$:

C, 46.87; H, 8.19; N, 7.45.

Found: C, 46.90; H, 8.13; N, 7.74.

The free acid was generated as described in Example 12. The acid is obtained as a white solid.

Anal. Calcd for $C_{21}H_{41}N_3O_3S_2 \cdot 2.3\ CF_3COOH$:

C, 43.31; H, 6.15; N, 5.92. Found:

C, 43.12; H, 6.19; N, 6.05.

Example 14

5(S)-[2(R)-amino-3-mercaptopropylamino]-6(S)-methyl-2(R)-benzyl-3,4-E-octenoyl-methionine, methyl ester and 5(S)-[2(R)-amino-3-mercaptopropyl-amino]-6(S)-methyl-2(R)-benzyl-3,4,E-octenoyl-methionine The titled compounds were prepared according to the methods of Example 1, substituting L-methionine methyl ester in Step E and benzyl-magnesium chloride in Step G. The octenoyl-methionine, methyl ester was obtained as white solid.

Anal. Calcd for $C_{25}H_{41}O_3N_3S_2 \cdot 3.3HCl$:

C, 48.74; H, 7.25; N, 6.82.

Found: C, 48.71; H, 7.16; N, 6.89.

The free acid was generated as described in Example 1, Step J.

Example 15

Preparation of 5(S)-[2(R)-amino-3-mercaptopropylamino]-6(S)-methyl-2(R)-n-propyl-octanoyl-homoserine lactone and 5(S)-[2(R)-amino-3-mercaptopropylamino]-6(S)-methyl-2(R)-n-propyl-octanoyl-homoserine The titled compounds were prepared exactly according to the methods of Example 1 with an additional catalytic hydrogenation step included between Step G and Step H as described in the following.

Step K. Preparation of 5(S)-N-tert-(butyloxy)carbonylamino-6(S)-methyl-2(R)-n-propyl-octanoyl-homoserine lactone A solution of 5(S)-N-tert-(butyloxy)carbonyl-amino-6(S)-methyl-2(R)-n-propyl-3,4-E-octenoyl-homoserine lactone (200 mg) in ethyl acetate (10 mL) was stirred under an atmosphere of hydrogen in the presence of 5% palladium on charcoal (20 mg) overnight. The resultant mixture was filtered, and the filtrate concentrated to provide quantitatively the hydrogenated product.

The lactone is obtained as a white solid.

Anal. Calcd for $C_{19}H_{37}O_3N_3S \cdot 2.35\ CF_3COOH$:

C, 43.42; H, 6.05; N, 6.41.

Found: C, 43.45; H, 5.81; N, 6.62.

The hydroxy-acid was generated in situ as described in Example 1, Step J.

Example 16

5(S)-[2(R)-amino-3-mercaptopropylamino]-6(S)-methyl-2(R)-benzyl-octanoyl-homoserine lactone and 5(S)-[2(R)-amino-3-mercapto-propylamino]-6(S)-methyl-2(R)-benzyl-octanoyl-homoserine The titled compounds were prepared according to the methods of Example 1, substituting benzylmagnesium chloride in Step G, and including an additional catalytic hydrogenation step as described in Example 15, Step K. The lactone is obtained as a white solid.

Anal. Calcd for $C_{23}H_{37}O_3N_3S \cdot 2.70\ CF_3COOH$:

C, 45.88; H, 5.38; N, 5.65.

Found: C, 45.90; H, 5.42; N, 5.83.

The hydroxy-acid was generated in situ as described in Example 1, Step J.

Example 17

In vitro inhibition of ras farnesyl transferase

The assay was conducted as described in Pompliano, et. al., Biochemistry 31, 3800 (1992) with the exception of utilizing recombinant human farnesyl transferase in place of the partially purified bovine enzyme described therein. The activity of the compounds of this invention is shown in Table 1.

TABLE 1

Inhibition of RAS farnesylation by compounds of this invention*

| Compound | ID$_{50}$ (nM) |
| --- | --- |
| 5(S)-[2(R)-amino-3-mercaptopropylamino]-6-methyl-2(R)-i-propyl-3,4-E-heptenoyl-homoserine | 5.0 |
| 5(S)-[2(R)-amino-3-mercaptopropylamino]-6-(S)-methyl-2(R)-i-propyl-3,4-E-octenoyl-homoserine | 3.5 |
| 5(S)-[2(R)-amino-3-mercaptopropylamino]-6-(S)-methyl-2(R)-benzyl-3,4-E-octenoyl-methionine | 1.9 |
| 5(S)-[2(R)-amino-3-mercaptopropylamino]-6-(S)-methyl-2(R)-n-butyl-3,4-E-octenoyl-homoserine | 1.5 |
| 5(S)-[2(R)-amino-3-mercaptopropylamino]-6-(S)-methyl-2(R)-i-propyl-3,4-E-octerioyl-methionine | 20.0 |
| 5(S)-[2(R)-amino-3-mercaptopropylamino]-6-(S)-methyl-2(R)-n-butyl-3,4-E-octenoyl-methionine | 2.5 |
| 5(S)-[2(R)-amino-3-mercaptopropylamino]-6-(S)-methyl-2(R)-n-propyl-3,4-E-octenoyl-homoserine | 4.0 |

*(IC$_{50}$ is the concentration of the test compound which gives 50% inhibition of FTase under the described assay conditions)

Example 18

In vivo ras farnesylation assay

The cell line used in this assay was the v-ras line, which expressed vital Ha-ras p21. The assay was performed essentially as described in DeClue, J. E. et. al., Cancer Research 51, 712–717, (1991). Cells in 10 cm dishes at 50–75% confluency were treated with the test compound (final concentration of solvent, methanol or dimethyl sulfoxide, was 0.1%). After 4 hours at 37° C., the cells were labelled in 3 ml methionine-free DMEM supplemeted with 10% regular DMEM, 2% fetal bovine serum and 400 μCi[$^{35}$S]methionine (1000 Ci/mmol). After an additional 20 hours, the cells were lysed in 1 ml lysis buffer (1% NP40/20 mMHEPES, pH 7.5/5 mM MgCl$_2$/1 mM DTT/10 μg/ml aprotinen/2 μg/ml leupeptin/2 μg/ml antipain/0.5 mM PMSF) and the lysates cleared by centrifugation at 100,000×g for 45 min. Aliqouts of lysates containing equal numbers of acid-precipitable counts were bought to 1 ml with IP buffer (lysis buffer lacking DTT) and immunoprecipitated with the ras-specific monoclonal antibody Y13-259 (Furth, M. E. et. al., J. Virol. 43, 294–304, (1982)). Following a 2 hour antibody incubation at 4° C., 200 μl of a 25% suspension of protein A-Sepharose coated with rabbit anti rat IgG was added for 45 min. The immunoprecipitates were washed four times with IP was buffer (20 nM HEPES, pH 7.5/1 mM EDTA/ 1% Triton X-100.0.5% deoxycholate/0.1%/SDS/0.1M NaCl) boiled in SDS-PAGE sample buffer and loaded on 13% acrylamide gels. When the dye front reached the bottom, the gel was fixed, soaked in Enlightening, dried and autoradiographed. The intensities of the bands corresponding to farnesylated and nonfarnesylated ras proteins were compared to determine the percent inhibition of farnesyl transfer to protein. Data for representative test compounds are tabulated in Table 2.

TABLE 2

Inhibition of Ras Farnesylation by the compounds of this invention in the v-ras cell line

| Compound | IC$_{50}$ (μM) |
|---|---|
| 5(S)-[2(R)-amino-3-mercaptopropylamino]-6-(S)-methyl-2(R)-i-propyl-3,4-E-octenoyl-homoserine lactone | 1–2.5 |
| 5(S)-[2(R)-amino-3-mercaptopropylamino]-6-(S)-methyl-2(R)-benzyl-3,4-E-octenoyl-homoserine lactone | 5–10 |
| 5(S)-[2(R)-amino-3-mercaptopropylamino]-6-(S)-methyl-2(R)-benzyl-3,4-E-octenoyl-methionine methyl ester | 1 |
| 5(S)-[2(R)-amino-3-mercaptopropylamino]-6-(S)-methyl-2(R)-n-butyl-3,4-E-octenoyl-methionine methyl ester | 1 |
| 5(S)-[2(R)-amino-3-mercaptopropylamino]-6-(S)-methyl-2(R)-i-propyl-3,4-E-octenoyl-methionine methyl ester | 0.1 |
| 5(S)-[2(R)-amino-3-mercaptopropylamino]-6-(S)-methyl-2(R)-i-propyl-3,4-E-heptanoyl-homoserine lactone | 1 |
| 5(S)-[2(R)-amino-3-mercaptopropylamino]-6-(S)-methyl-2(R)-n-propyl-3,4-E-octenoyl-homoserine lactone | 5 |

What is claimed is:

1. A compound which inhibits farnesyl - protein transferase of the formula I:

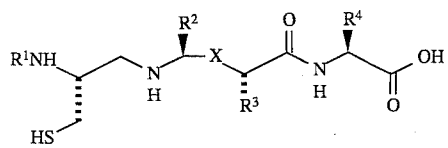

wherein:

R$^1$ is hydrogen, an alkyl group, an aralkyl group an acyl group, an aracyl group, an aroyl group, an alkylsulfonyl group, aralkylsulfonyl group or arylsulfonyl group, wherein the alkyl and the alkyl portion of the aryl is a straight chain or branched chain hydrocarbons of 1 to 6 carbon atoms;

R$^2$, R$^3$ and R$^4$ are independently selected from
 a) a side chain of naturally occurring amino acids;
 b) a side chain of oxidized forms of naturally occurring amino acids selected from:
  i) methionine sulfoxide or
  ii) methionine sulfone; or
 c) a aliphatic group selected from:
  i) allyl,
  ii) cyclohexyl, and
  iii) a branched or unbranched sturated chain of 2 to 8 carbons;
   wherein the aliphatic group is optionally substituted with an aromatic or heteroaromatic ring;
 d) phenyl, and
 e) a heteroaromatic group selected from pyridyl and imidazolyl;

X is CH$_2$CH$_2$ or trans CH=CH;
and the pharmaceutically acceptable salts thereof.

2. A compound which inhibits farnesyl protein transferase which is:

5(S)-[2(R)-amino-3-mercaptopropylamino]-6(S)-methyl-2(R)-n-butyl-3,4-E-octenoyl-methionine, 5(S)-[2(R )-amino-3-mercaptopropylamino]-6(S)-methyl-2(R)-isopropyl-3,4-E-octenoyl-methionine, or 5(S)-[2(R)-amino-3-mercaptopropylamino ]-6(S)-methyl-2(R)-benzyl-3,4-E-octenoyl-methionine, or a pharmaceutically acceptable salt or disulfide thereof.

3. The compound of claim 2 which 5(S)-[2(R)-amino-3-mercaptopropylamino]-6(S)-methyl-2(R)-benzyl-3,4-E-octenoyl-methionine

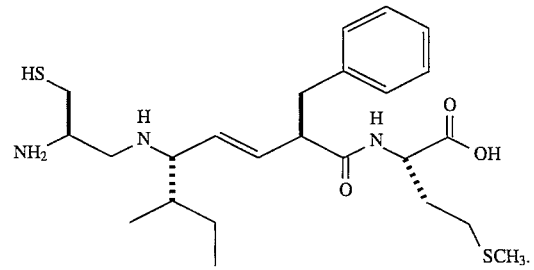

4. The compound of claim 2 which is:
5(S)-[2(R)-amino-3-mercaptopropylamino]-6(S)-methyl-2(R)-n-butyl-3,4-E-octenoyl-methionine

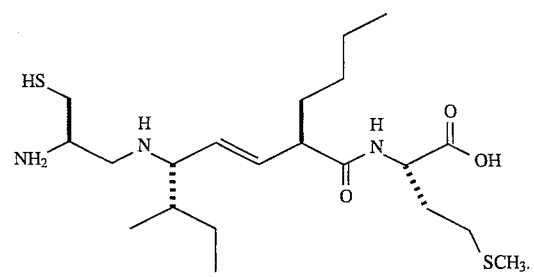

5. The compound of claim 2 which is: 5(S)-[2(R)-amino-3-mercaptopropylamino]-6(S)-methyl-2(R)-i-propyl-3,4-E-octenoyl-methionine

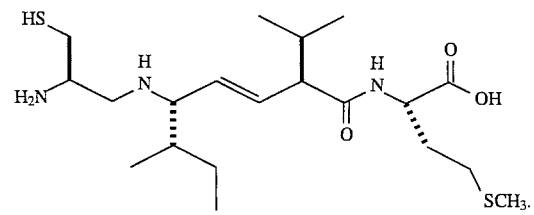

* * * * *

UNITED STATES PATENT AND TRADEMARK OFFICE
CERTIFICATE OF CORRECTION

PATENT NO. : 5,504,212

DATED : Apr. 2, 1996

INVENTOR(S) : S. Jane de Solms, Samuel L. Graham and John S. Wai

It is certified that error appears in the above-identified patent and that said Letters Patent is hereby corrected as shown below:

At Column 21, line 61, should read as follows:

wherein the alkyl and the alkyl portion of the acyl is a .

...

Signed and Sealed this

Eighth Day of October, 1996

Attest:

BRUCE LEHMAN

*Attesting Officer*    *Commissioner of Patents and Trademarks*